(12) United States Patent
Petersen et al.

(10) Patent No.: US 11,964,070 B2
(45) Date of Patent: Apr. 23, 2024

(54) DISINFECTANT AND SANITIZER CANISTER SYSTEM AND METERING DEVICE FOR SYSTEM

(71) Applicant: Quin Global US, Inc., Omaha, NE (US)

(72) Inventors: Matthew Petersen, Omaha, NE (US); Carl Fowler, Perth (GB); Jayden Earl, Quean Beyn (AU)

(73) Assignee: QUIN GLOBAL US, INC., Omaha, NE (US)

( * ) Notice: Subject to any disclaimer, the term of this patent is extended or adjusted under 35 U.S.C. 154(b) by 338 days.

(21) Appl. No.: 17/342,955

(22) Filed: Jun. 9, 2021

(65) Prior Publication Data

US 2021/0379226 A1    Dec. 9, 2021

Related U.S. Application Data

(60) Provisional application No. 63/036,633, filed on Jun. 9, 2020.

(51) Int. Cl.
| | |
|---|---|
| *A61L 2/22* | (2006.01) |
| *A61L 2/26* | (2006.01) |

(Continued)

(52) U.S. Cl.
CPC ................. *A61L 2/22* (2013.01); *A61L 2/26* (2013.01); *B05B 9/01* (2013.01); *B05B 9/04* (2013.01);
(Continued)

(58) Field of Classification Search
CPC .......... A61L 2/22; A61L 2/26; A61L 2101/32; A61L 2202/15; A61L 2202/17;
(Continued)

(56) References Cited

U.S. PATENT DOCUMENTS

| | | | | |
|---|---|---|---|---|
| 3,013,591 A | * | 12/1961 | Stanley ................. | B65B 31/003 222/335 |
| 3,229,855 A | * | 1/1966 | Eggert, Jr. ............ | B05B 7/1673 92/194 |

(Continued)

FOREIGN PATENT DOCUMENTS

| | | |
|---|---|---|
| AU | 1984025049 A1 | 9/1984 |
| BR | 112012027105 A2 | 7/2016 |

(Continued)

*Primary Examiner* — Paul R Durand
*Assistant Examiner* — Michael J. Melaragno
(74) *Attorney, Agent, or Firm* — Suiter Swantz IP

(57) ABSTRACT

A disinfectant and sanitizer canister system is disclosed. The system may include a pre-pressurized canister being pre-filled with one or more liquid cleaners and one or more propellants. The system may further include a valve sub-system including a dispensing valve and a valve control mechanism. The control mechanism may be configured to regulate the pressure of the pre-pressurized canister to cause the pre-pressurized canister to release the one or more liquid cleaners. The system may further include a dispensing sub-system configured to fluidically couple the pre-pressurized canister to the valve sub-system. The dispensing sub-system may include a dispensing member configured to dispense the one or more liquid cleaners contained within the pressurized canister. The system may further include a metering device, the metering device configured to provide a predetermined amount of pressure to dispense a predetermined metered dose of the one or more liquid cleaners.

19 Claims, 9 Drawing Sheets

(51) Int. Cl.
*A61L 101/32* (2006.01)
*B05B 9/00* (2006.01)
*B05B 9/01* (2006.01)
*B05B 9/04* (2006.01)
*B05B 12/00* (2018.01)
*C11D 7/32* (2006.01)
*C11D 17/00* (2006.01)

(52) U.S. Cl.
CPC .......... *B05B 12/002* (2013.01); *C11D 7/3209* (2013.01); *C11D 17/0043* (2013.01); *A61L 2101/32* (2020.08); *A61L 2202/15* (2013.01); *A61L 2202/17* (2013.01); *B05B 9/007* (2013.01)

(58) Field of Classification Search
CPC ........... B05B 9/01; B05B 9/04; B05B 12/002; C11D 7/3209; C11D 17/0043
See application file for complete search history.

(56) References Cited

U.S. PATENT DOCUMENTS

| | | | |
|---|---|---|---|
| 3,469,788 A * | 9/1969 | Glaros | B05B 9/04 222/399 |
| 3,797,507 A * | 3/1974 | Jackson | F02B 77/04 134/102.1 |
| 3,832,459 A | 8/1974 | Berkeley | |
| 3,844,449 A | 10/1974 | Alter | |
| 4,787,537 A * | 11/1988 | Hau | B05B 9/01 222/496 |
| 5,020,689 A * | 6/1991 | Eitner, Jr. | A01M 1/2044 222/630 |
| 5,088,517 A * | 2/1992 | Bersch | B08B 9/032 222/162 |
| 5,529,713 A | 6/1996 | Gauthier-Fournier | |
| 7,901,642 B2 * | 3/2011 | Ono | A61L 2/26 134/102.2 |
| 8,123,956 B2 | 2/2012 | King et al. | |
| 8,178,078 B2 * | 5/2012 | Clark | A01N 43/38 424/45 |
| 8,459,509 B2 | 6/2013 | Bui | |
| 9,044,414 B2 * | 6/2015 | Clark | A61K 8/604 |
| 9,364,007 B2 * | 6/2016 | Clark | A61Q 19/00 |
| 9,730,558 B2 | 8/2017 | McNulty et al. | |
| 9,833,803 B2 | 12/2017 | Hart | |
| 9,943,080 B2 | 4/2018 | Cohen et al. | |
| 2005/0263208 A1 * | 12/2005 | MacNeal | F16K 1/302 141/301 |
| 2006/0048820 A1 * | 3/2006 | Horner | B08B 3/026 137/382 |
| 2006/0102245 A1 * | 5/2006 | Kaechle | B05B 9/0833 239/526 |
| 2007/0267518 A1 | 11/2007 | Darling et al. | |
| 2009/0311195 A1 * | 12/2009 | Clark | A61K 8/922 512/1 |
| 2011/0014093 A1 * | 1/2011 | Ono | A61L 2/18 422/292 |
| 2011/0036929 A1 | 2/2011 | Hudson et al. | |
| 2011/0147407 A1 * | 6/2011 | Calio | B08B 3/026 222/394 |
| 2012/0213711 A1 * | 8/2012 | Clark | A01N 65/12 512/1 |
| 2014/0251006 A1 | 9/2014 | Freudenberg et al. | |
| 2015/0166251 A1 | 6/2015 | Jones | |
| 2015/0181891 A1 * | 7/2015 | Clark | A61K 8/604 514/521 |
| 2016/0002023 A1 | 1/2016 | Chen et al. | |
| 2016/0016721 A1 | 1/2016 | Rhea et al. | |
| 2016/0136672 A1 * | 5/2016 | Doswell | B05B 15/70 239/11 |
| 2018/0280905 A1 | 10/2018 | Orsita et al. | |
| 2018/0353632 A1 | 12/2018 | Divisi | |
| 2019/0192892 A1 * | 6/2019 | Johnson | A62C 35/13 |
| 2020/0292366 A1 | 9/2020 | Ophardt et al. | |
| 2020/0360553 A1 | 11/2020 | Satoh et al. | |
| 2021/0069363 A1 * | 3/2021 | Zimak | A61L 2/24 |
| 2021/0379226 A1 * | 12/2021 | Petersen | C11D 7/3209 |
| 2022/0290016 A1 * | 9/2022 | Fowler | B65D 83/752 |

FOREIGN PATENT DOCUMENTS

| | | | |
|---|---|---|---|
| CA | 2813118 C | 10/2018 | |
| CN | 111453684 A | 7/2020 | |
| DE | 3714699 A1 | 1/1988 | |
| EP | 0396223 A3 | 9/1991 | |
| EP | 1125896 A | 8/2001 | |
| EP | 2428280 A3 | 10/2013 | |
| EP | 2227215 B1 | 4/2017 | |
| EP | 3685823 A1 | 7/2020 | |
| EP | 3799962 A1 | 4/2021 | |
| ES | 2672998 | 6/2018 | |
| ES | 2675234 | 7/2018 | |
| GB | 645917 A | 11/1950 | |
| GB | 2074048 B | 12/1983 | |
| IL | 263964 A | 1/2019 | |
| JP | WO2019098042 A1 | 11/2020 | |
| KR | 200337897 Y1 | 1/2004 | |
| KR | 100757993 B1 | 9/2007 | |
| KR | 101237458 B1 | 2/2013 | |
| WO | 2010028455 A1 | 3/2010 | |
| WO | 2013010000 A2 | 1/2013 | |
| WO | WO-2021252658 A1 * | 12/2021 | A61L 2/22 |

* cited by examiner

DISINFECTANT AND SANITIZER CANISTER SYSTEM AND METERING DEVICE FOR SYSTEM

CROSS-REFERENCE TO RELATED APPLICATIONS

The present disclosure claims the benefit under 35 U.S.C. § 119(e) of U.S. Provisional Application Ser. No. 63/036,633, filed Jun. 9, 2020, entitled DISINFECTANT AND SANITIZER CANISTER SYSTEM AND METERING DEVICE FOR SYSTEM, naming Matthew Petersen as inventor, which is incorporated herein by reference in the entirety.

TECHNICAL FIELD

The present disclosure generally relates to the field of disinfecting and sanitizing; and more particularly to a disinfectant and sanitizer canister system configured for dispensing one or more disinfectants and/or sanitizers contained within a pressurized canister of the canister system and a metering device for such system.

BACKGROUND

The use of sanitizers and/or disinfectants has grown exponentially in recent months and along with it has come a shortage of the traditional methods of dispensing and a shortage of the products themselves. Often it is desirable to quickly and easily disinfect and/or sanitize a variety of surfaces to kill a variety of a viruses and pathogens that may be on such surfaces. For example, it may be desirable to disinfect and/or sanitize a variety of surfaces within an office space or building to prevent the spread of a virus among those utilizing the office space or building. However, it is often difficult to disinfect and/or sanitize such areas because of the amount and size of the surfaces. Conventional disinfecting and/or sanitizing techniques are inefficient and require a lot of time and energy. Further, there is a growing need for large amounts of sanitizer and/or disinfectants to be dispensed in areas that do not have electrical power.

SUMMARY

A disinfectant and sanitizer canister system is disclosed. The system may include a pre-pressurized canister being pre-filled with one or more liquid cleaners and one or more propellants. The system may further include a valve sub-system including a dispensing valve and a valve control mechanism. The control mechanism may be configured to regulate the pressure of the pre-pressurized canister to cause the pre-pressurized canister to release the one or more liquid cleaners. The system may further include a dispensing sub-system configured to fluidically couple the pre-pressurized canister to the valve sub-system. The dispensing sub-system may include a dispensing member configured to dispense the one or more liquid cleaners contained within the pressurized canister. The system may further include a metering device, the metering device configured to dispense a predetermined metered dose of the one or more liquid cleaners.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION

Figure 1:
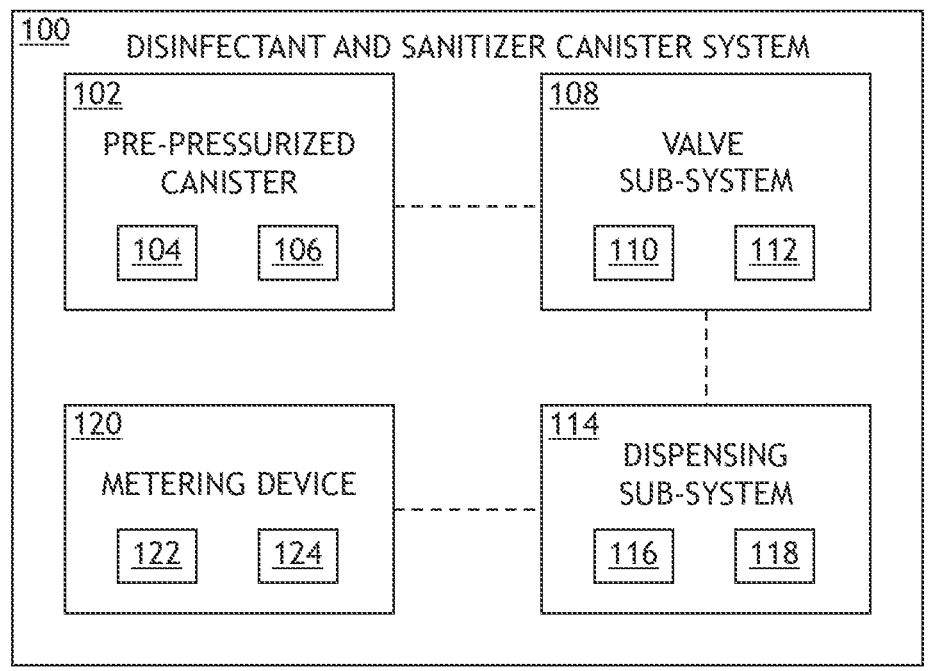
FIG. 1 illustrates a simplified block diagram of the system, in accordance with one or more embodiments of the present disclosure.

The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Reference will now be made in detail to the subject matter disclosed, which is illustrated in the accompanying drawings.

Embodiments of the present disclosure are directed to a disinfectant and sanitizing canister system for quickly and easily disinfecting and/or sanitizing one or more areas. The canister system may be used to disinfect and/or sanitize one or more areas within a commercial building such as, but not limited to, an office building, workspace, retail building, or the like. The canister system may also be used to disinfect and/or sanitize one or more areas within a non-commercial building such as, but not limited to, a residential area (e.g., homes, or the like). Further, the canister system may be used to disinfect and/or sanitize various surfaces including, but not limited to, body parts (e.g., hands), non-porous surfaces, porous surfaces, fabrics, or the like. For instance, the canister system may be used as a hand sanitizer apparatus.

FIGS. 1-8 generally illustrate a disinfectant and sanitizer canister system 100, in accordance with one or more embodiments of the present disclosure.

The canister system 100 may include a pressurized canister 102. For example, the pressurized canister 102 may include a pre-pressurized canister. For purposes of the present disclosure, the term "pre-pressurized" may mean a canister that is pressurized and filled with the desired contents (e.g., cleaner and propellant) prior to sealing the canister for use. It is noted that the pre-pressurized canister 102 may eliminate the need for a compressor to reduce the weight of the system 100 to allow for easy transportation. Further, it is noted that the pre-pressurized canister 102 may eliminate the need for an external power source to operate the system (e.g., air, electricity, or the like). This allows the canister system 100 to be used in areas that are not easily accessible to power sources such as, but not limited to, athletic fields, sporting events, convention centers, large warehouses, schools, office buildings, retail stores, grocery stores, or the like.

The pressurized canister 102 may be configured to contain one or more liquid cleaners 104. The pressurized canister 102 may further be configured to contain one or more propellants 106. For example, the pressurized canister 102 may include 5% by weight propellant.

It is contemplated herein that the pressurized canister 102 may contain any percentage (or ratio) of the one or more liquid cleaners 104 and the one or more propellants 106. For example, the pressurized canister 102 may include between 30% and 90% liquid cleaner by volume, and 10% to 70% propellant by volume. For instance, the pressurized canister 102 may include 50% liquid cleaner by volume and 50% propellant by volume. In another instance, the pressurized canister 102 may include 65% liquid cleaner by volume and 45% propellant by volume. For purposes of the present disclosure, the term "disinfectant," "sanitizer," "disinfectant/sanitizer," or variants thereof may refer to the mixture of the one or more liquid cleaners and the one or more propellants.

It is noted herein that the pressurized canister 102 may include any amount of pressure suitable for dispensing the disinfectant/sanitizer. For example, the pressurized canister 102 may be pre-pressurized at 10 PSI. Further, it is noted herein that the pressurized canister 102 may be any size. For example, the pressurized canister may be 22.0 Liters. By way of another example, the pressurized canister may be 7.0 Liters.

The one or more liquid cleaners may include any disinfectant, sanitizer (e.g., hand sanitizer, surface sanitizer), soap, surface cleaner, or the like known in the art suitable for killing viruses, bacteria, fungus, pathogens, and the like. Further, the one or more liquid cleaners may include any base of liquid cleaner known in the art including, but not limited to, one or more water-based cleaners, one or more alcohol-based cleaners, or one or more solvent-based liquid cleaners. For example, the one or more liquid cleaners may include, but are not limited to, didecyldimethylammonium chloride (DDAC), alcohols, quaternary ammonium, sodium hypochlorite (bleach), chlorines, peroxides, phenolics, peroxy and peroxo acids, oxidizing agents, or the like. The liquid cleaners may have one or more functions including, but not limited to, cleaning, disinfecting, antimicrobial, antibacterial, antiviral, fungicidal, mildewcidal, or the like. Further, the liquid cleaners may be configured as corrosion inhibits and be configured to protect one or more metal surfaces after the liquid cleaner is applied. Therefore, reference to disinfectant/sanitizers should not be construed as a limitation on the present disclosure.

The one or more propellants may include any propellant known in the art. For example, the one or more propellants may include, but are not limited to, one or more inert gases, one or more liquefied gases, carbon dioxide, nitrogen gas, nitrous oxide, propane, dimethyl ether, HFA (hydrofluoroalkane) 134a (1,1,1,2-tetrafluoroethane), HFO (hyrdrofluoroolefin) 1234ze (1,3,3,3,3-tetrafluoroprop-1-ene), HFC (hydrofluorocarbon) 152A (1,1-difleuoroethane), or the like.

The canister system 100 may include a valve sub-system 108. The valve sub-system 108 may include dispensing valve 110. For example, the dispensing valve 110 may include a threaded fitting. By way of another example, the dispensing valve 110 may include a quick connect fitting. The dispensing valve 110 may couple to a portion of the dispensing sub-system 114 to dispense the disinfectant/sanitizer. Further, the valve sub-system 108 may couple to the pressurized canister 102 via any mechanism known in the art suitable for pressurized canisters.

The valve sub-system 108 may further include a knob or lever 112 configured to regulate the pressure of pressurized canister 102 such that the disinfectant/sanitizer contained within the canister 102 may be released. The valve sub-system 108 may further include a cap or stop configured to prevent the dispensing valve 110 from leaking.

Figure 2A:
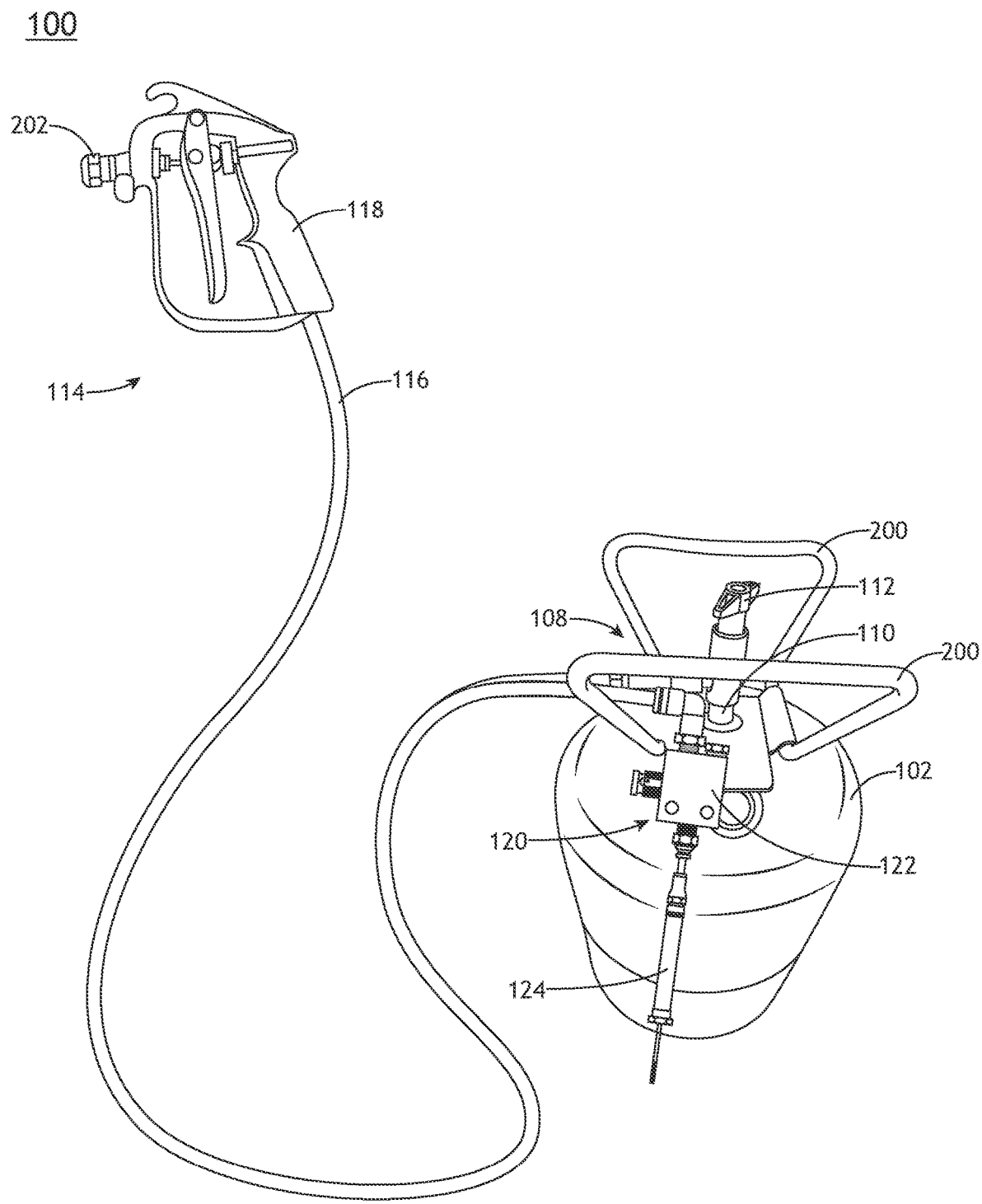
FIG. 2A illustrates a perspective view of the system, in accordance with one or more embodiments of the present disclosure.
Figure 2B:
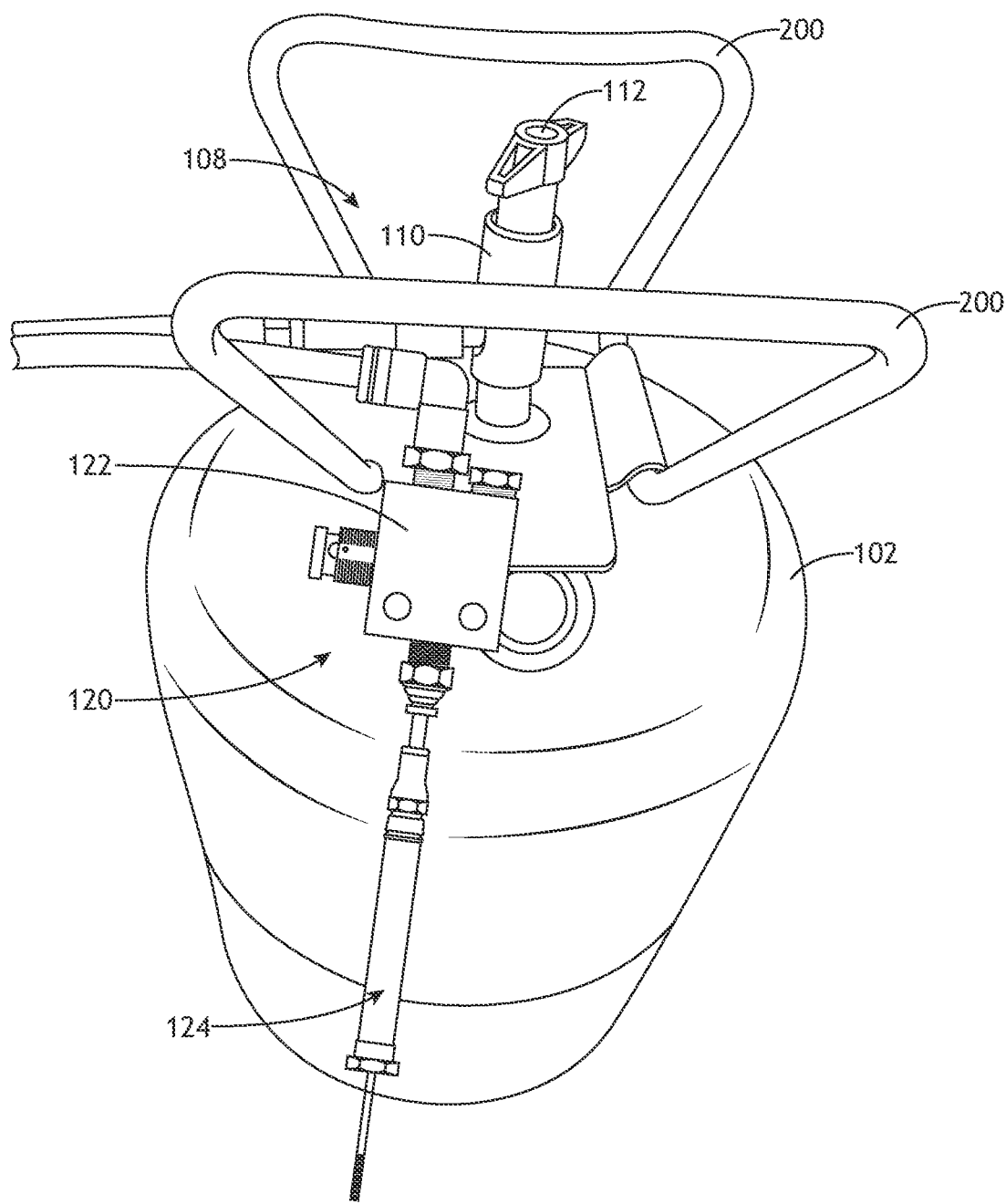
FIG. 2B illustrates a top perspective view of the system, in accordance with one or more embodiments of the present disclosure.

Although FIGS. 2A-2B illustrates a specific valve assembly it is noted herein that the valve assembly may include any valve assembly known in the art of pressurized canisters.

The canister system 100 may include a dispensing sub-system 114 configured to couple to a portion of the valve sub-system 108. The dispensing sub-system 114 may include a dispensing hose 116 and a dispensing member 118. For example, a proximate end of the dispensing hose 116 may couple to the valve sub-system 108 and a distal end of the dispensing hose 116 may couple to the dispensing member 118, such that the one or more liquid cleaners and the one or more propellants may be dispensed through a portion of the dispensing member 118 to disinfect and/or sanitize a desired area. The dispensing hose 116 may be formed of any material known in the art. For example, the dispensing hose 116 may be formed of, but is not required to be formed of, rubber, nylon, Teflon™, polyethylene, polypropylene, or the like.

Further, the dispensing sub-system 114 may include a dispensing member 118 configured to directly couple to a portion of the valve sub-system 108.

The one or more liquid cleaners configured to exit the pre-pressurized canister via the dispensing hose when the dispensing member dispenses the one or more liquid cleaners. The dispensing sub-system 114 may be configured to dispense the disinfectant/sanitizer using any technique known in the art. For example, the dispensing sub-system 114 may dispense the disinfectant/sanitizer via spraying, liquid stream, fogging, misting, electrostatic transfer, or the like.

Figure 3:
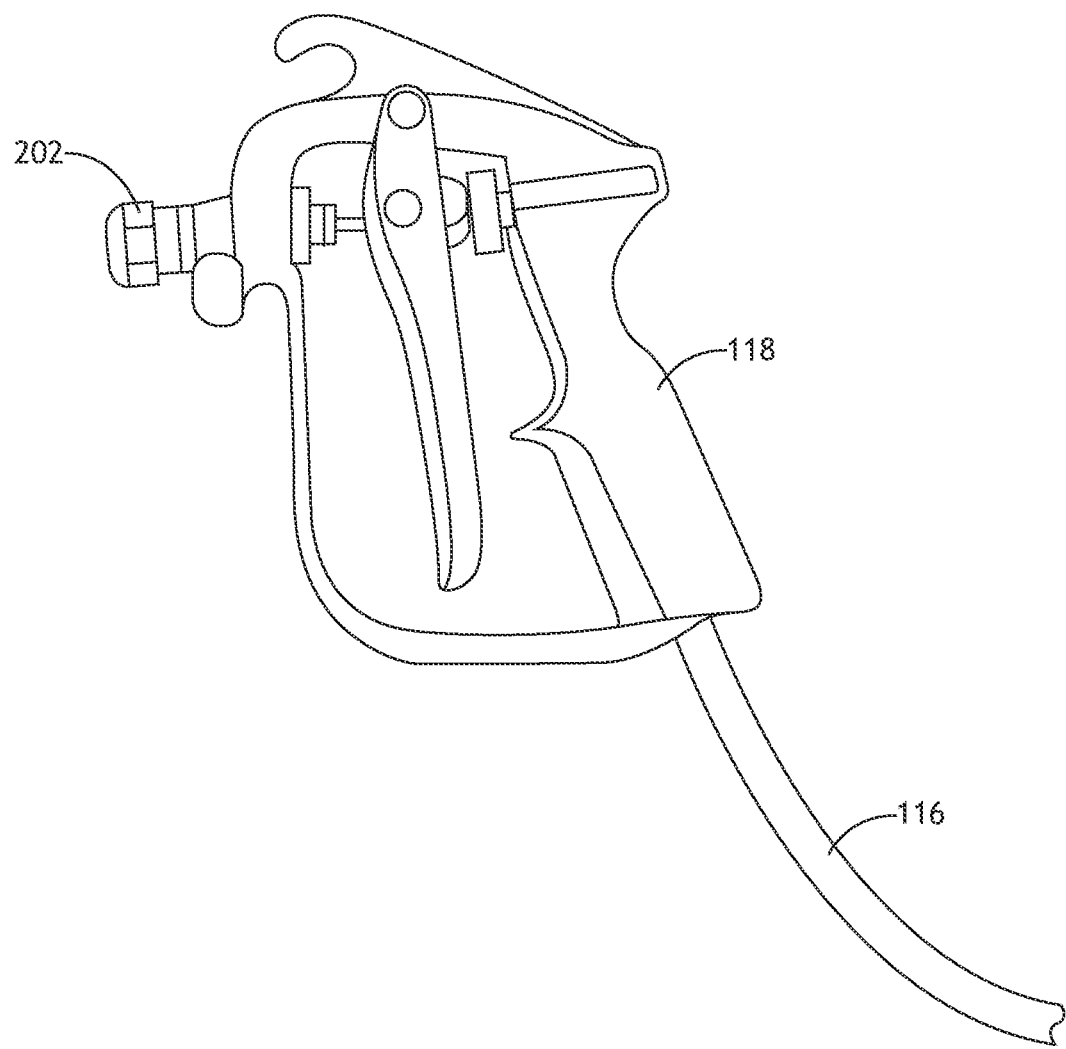
FIG. 3 illustrates a dispensing sub-system of the system, in accordance with one or more embodiments of the present disclosure.

The dispensing sub-system 114 may include any dispensing member 118 known in the art. For example, as shown in FIG. 3, the dispensing sub-system 114 may include a spray gun (e.g., gunjet spray gun). By way of another example, the dispensing sub-system 114 may include a ball valve. By way of another example, the dispensing sub-system 114 may include a thumb trigger valve. By way of another example, the dispensing sub-system 114 may include an air-operated valve. By way of another example, the dispensing sub-system 114 may include a solenoid operated valve. It is noted herein that the dispensing sub-system 114 may include any dispensing member, therefore the above discussion should not limit the scope of present disclosure.

The dispensing sub-system 114 may further include one or more dispensing tips 202. For example, the dispensing sub-system 114 may include, but is not required to include, one or more flat fan tips, cone spray tips, stream control tips, parabolic spay tips, or the like.

The control of the dispensing may occur in serval different ways. For example, the spray application may be manual via a spray gun (e.g., the spray gun shown in FIG. 3) or a wand. By way of another example, the spray (or stream) application may be automated via an electronic eye, electronic controller, solenoid valve, or the like. By way of another example, the dispensing may be operated via a foot-pedal operation using a mechanism connecting the foot pedal to the dispensing valve of the dispensing sub-system 114. By way of a further example, the dispensing may be operated via lever actuation using an object (e.g., a hand, or the like) to pass under the dispensing member 118 of the dispensing sub-system 114.

The canister system 100 may include a metering device 120 configured to allow a predetermined metered dose of liquid cleaner or sanitizer to be dispensed. The metering device 120 may include a multi-directional valve sub-system 122 and a metered cylinder 124.

Figure 4:
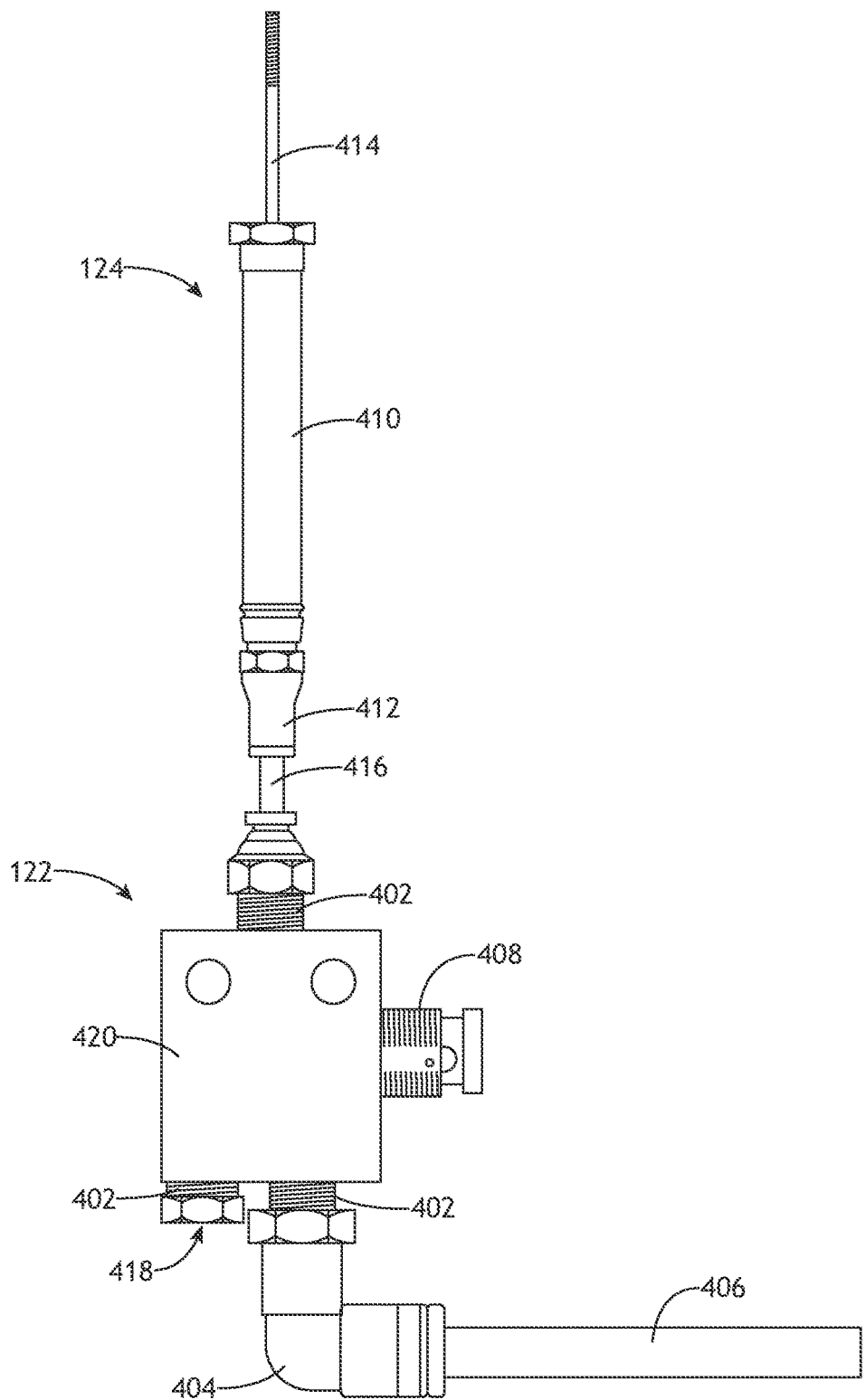
FIG. 4 illustrates a metering device of the system, in accordance with one or more embodiments of the present disclosure.

Referring to FIG. 4, the multi-directional valve assembly 122 may include a three-way directional value assembly 400. The three-way directional valve assembly 400 may include one or more valves 402. For example, the three-way directional valve assembly 400 may include a first valve 402, a second valve 402, and a third valve 402. The one or more valves 402 may include any input port known in the art including, but not limited to, an ⅛ NPT (F) input port configured to couple to a variety of fittings.

At least one of the one or more valves 402 of the multi-directional valve assembly 400 may be configured to couple to a portion of the canister system 100. For example, as shown in FIG. 4, the first valve 402 may couple to a connector 404 of a hose line 406. The hose line 406 may couple to the dispensing sub-system 114 of the canister system 100. The connector 404 may include any type of connector known in the art including, but not limited to, an elbow connector 404.

The multi-directional valve assembly 122 may include an actuator 408. The actuator 408 may be configured control the multi-directional valve assembly 122. The actuator 408 may include any type of actuator known in the art including, but not limited to, a push-button control actuator, a lever, or the like. For example, as shown in FIG. 4, the multi-directional valve assembly 400 may include a push-button control actuator 408.

Although FIG. 4 illustrates the actuator as a manual actuator, it is noted that the multi-directional valve assembly 122 may be operated either manually or electronically. For example, the multi-directional valve assembly 122 may be operated by an air source. By way of another example, the multi-directional valve assembly 122 may be operated by a power source.

The multi-directional valve assembly 122 may include a discharge port 418. The discharge port 418 may be configured discharge the metered material through the discharge port.

The metering device 120 may include a metered cylinder 124. For example, the metering device 120 may include a spring return air cylinder 124.

The metered cylinder 410 may include a liquid side 412. The liquid side 412 may include any volumetric capacity. For example, the liquid side 412 may have a volumetric capacity between 1.0 and 2.5 mL.

The metered cylinder 410 may include a spring side 414. The spring side 414 may have any amount of pressure sufficient to dispense a predetermined metered dose of liquid (e.g., the disinfectant and/or sanitizer).

Figure 5:
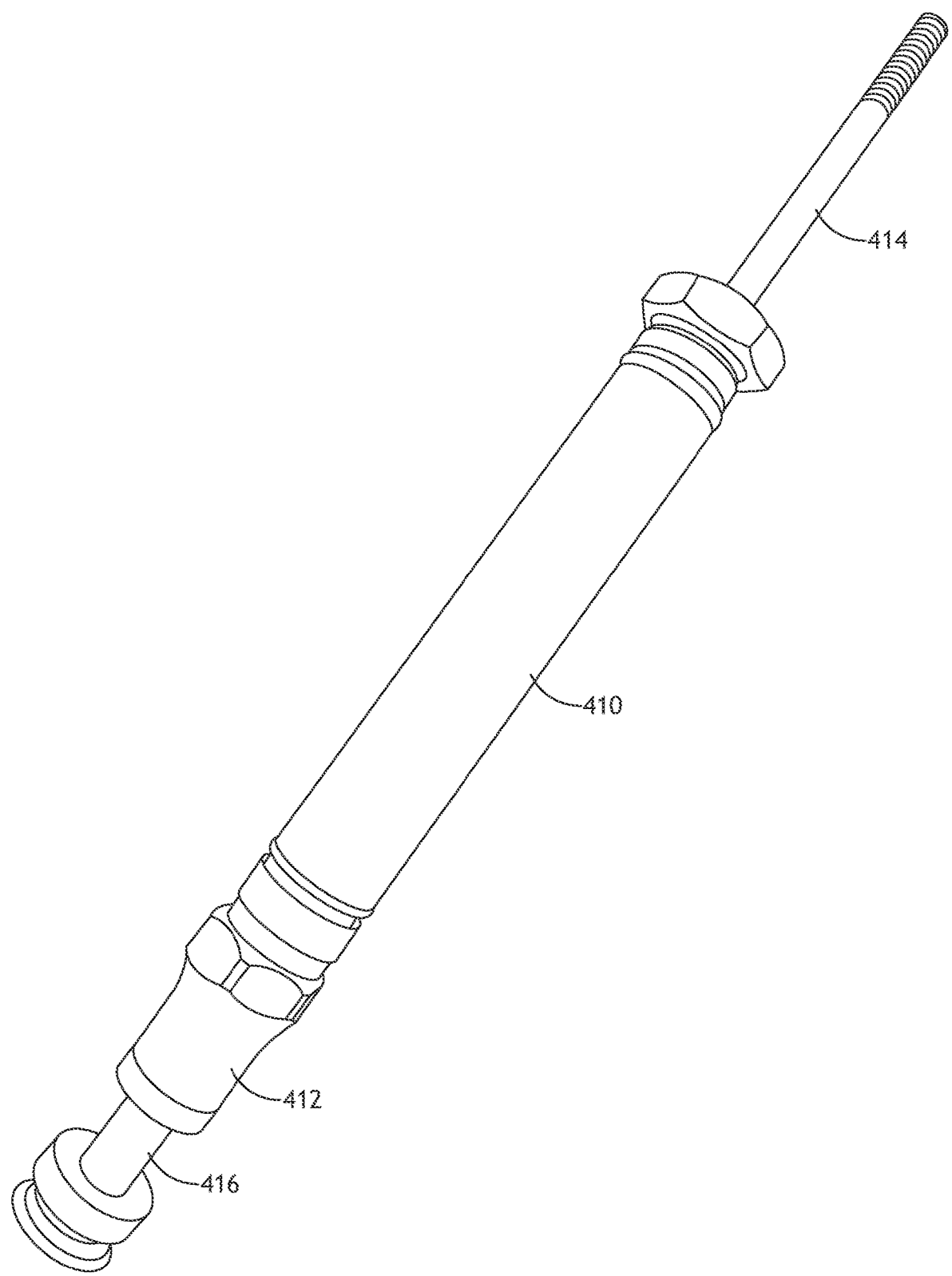
FIG. 5 illustrates a metered cylinder of the metering sub-system, in accordance with one or more embodiments of the present disclosure.
Figure 6:
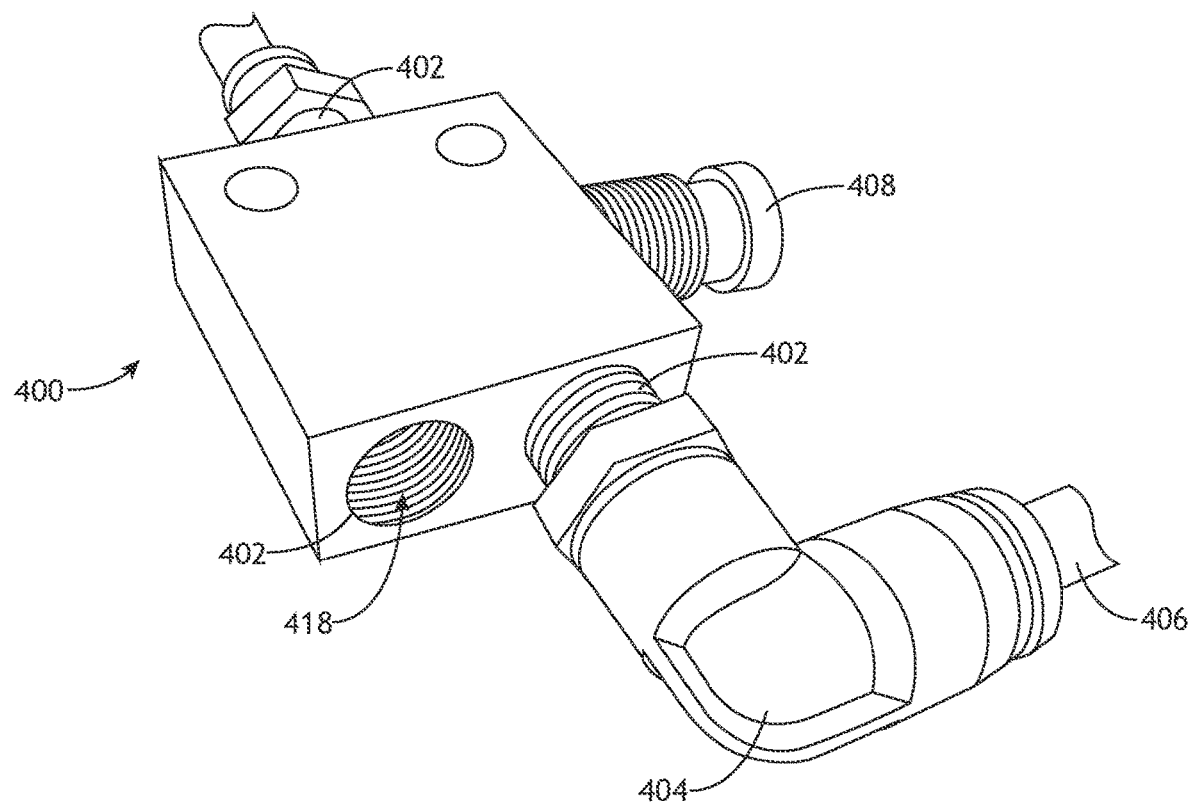
FIG. 6 illustrates a multi-directional valve sub-system for the metering sub-system, in accordance with one or more embodiments of the present disclosure.

Referring to FIG. 4-6, the metering device 120 may further include one or more seals 416. The one or more seals 416 may be configured to couple the metered cylinder 410 to the multi-directional valve assembly 122. For example, the one or more seals 416 may couple to the liquid side 412 of the metered cylinder 410 and a valve of the one or more valves 402. The one or more seals 416 may be resistant to one or more chemicals of the one or more liquid cleaners. For example, the one or more seals 416 may be resistant to one or more chemicals used in the one or more liquid cleaners.

During operation, the metering device 120 may be configured to allow flow from the pressurized canister 102, through the valve 402, and into the liquid side 412 of the metering cylinder 124 when in the "rest" or "normal" position. When the actuator is engaged, the valve 402 redirects flow from the metering cylinder 124 out the discharge port 418. When the actuator 408 is released, the valve 402 returns to the normal position, allowing the flow from the pressurized canister 102 to enter the metering cylinder 124, and refill the cylinder 124. The spring in the spring side 414 of the metering cylinder 124 maintains the pressure that causes the dispense from the discharge port 418. It is noted herein that although FIGS. 4-6 illustrate a three-way directional valve assembly 400, it is noted herein that the metering device 120 may include any multi-directional valve assembly known in the art. Therefore, the configuration depicted in FIGS. 4-6 should not be construed as limiting the scope of the present disclosure.

Referring back to FIG. 2, the canister system 100 may include one or more handles 200. The one or more handles 200 may be configured to allow a user to easily transport the canister system 100. Although FIG. 2 illustrates a specific size, shape, and configuration of the one or more handles 200, it is contemplated that the canister system 100 may include any size, shape, and/or configuration of the one or more handles 200.

Figure 7:
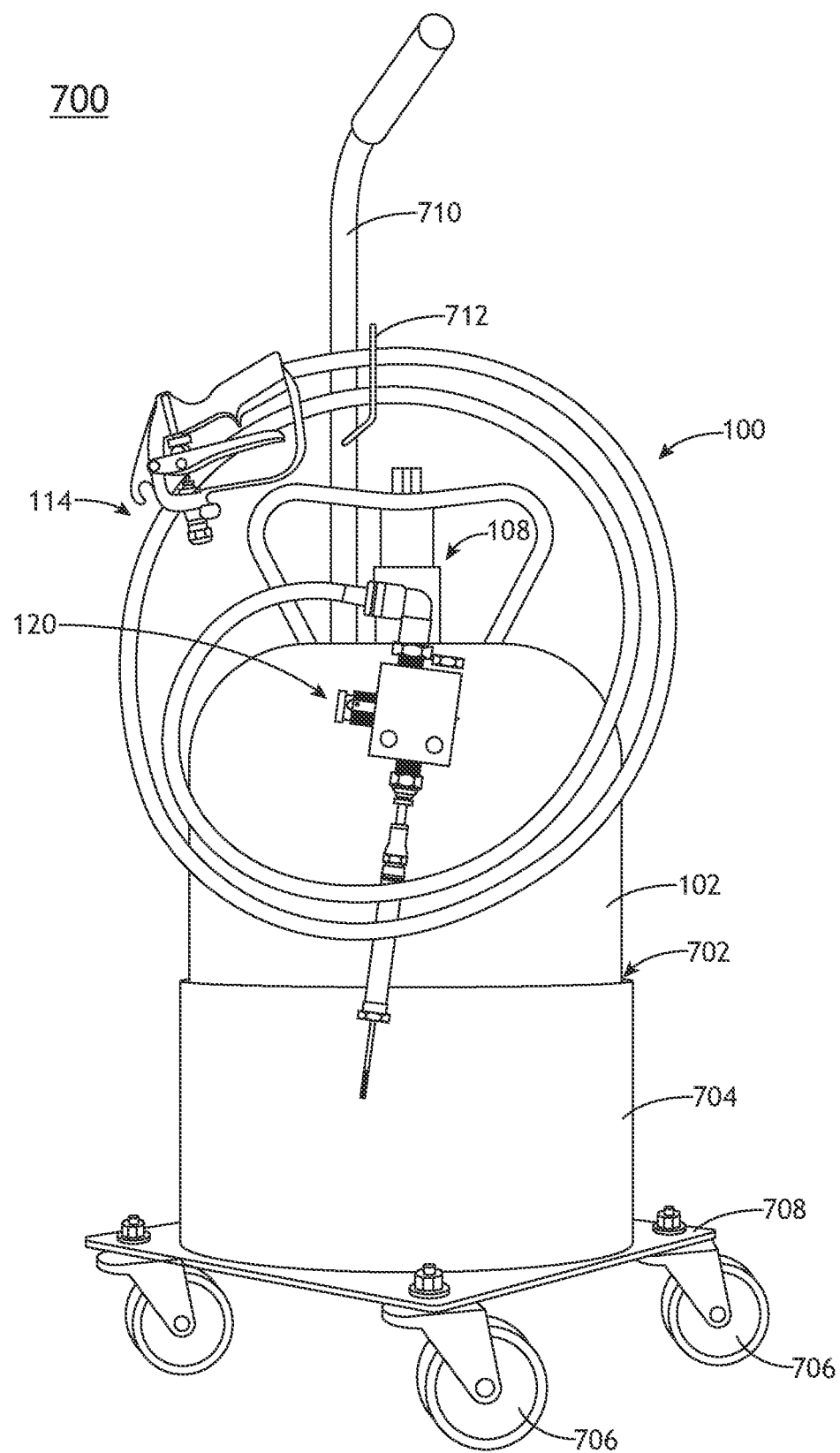
FIG. 7 illustrates a trolley for the system, in accordance with one or more embodiments of the present disclosure.

Referring to FIG. 7, the canister system 100 may be configured to couple to a trolley assembly 700 configured to aid in transporting the canister 102.

The trolley assembly 700 may include a cavity 702 defined by one or more sidewalls 704. The cavity 702 may be configured to house the canister system 100. For example, the shape of the cavity 702 may be complementary to the shape of the canister 102 of the system 100.

The trolley assembly 700 may further include one or more wheels 706 coupled to a base 708 of the trolley assembly 700. The one or more wheels 706 may be configured to allow a user to easily transport the canister system 100 around to the one or more desired areas.

The trolley assembly 700 may further include a handle 710 coupled to the base 708 of the trolley assembly 700. The handle 710 may also be coupled to a portion of the sidewall 704 of the trolley assembly 700. The handle 710 may allow a user to transport the trolley assembly including the canister system 100 to one or more desired areas. The handle 710 may further include one or more grip bands. For example, the handle 710 may include one or more non-slip grip bands.

The handle 710 may include one or more hooks 712 configured to hold a portion of the dispensing sub-system 114. For example, the dispensing hose 116 of the dispensing sub-system 114 may couple to the one or more hooks 712 such that the dispensing hose 116 does not interfere with the transportation or use of the canister system 100.

Figure 8:
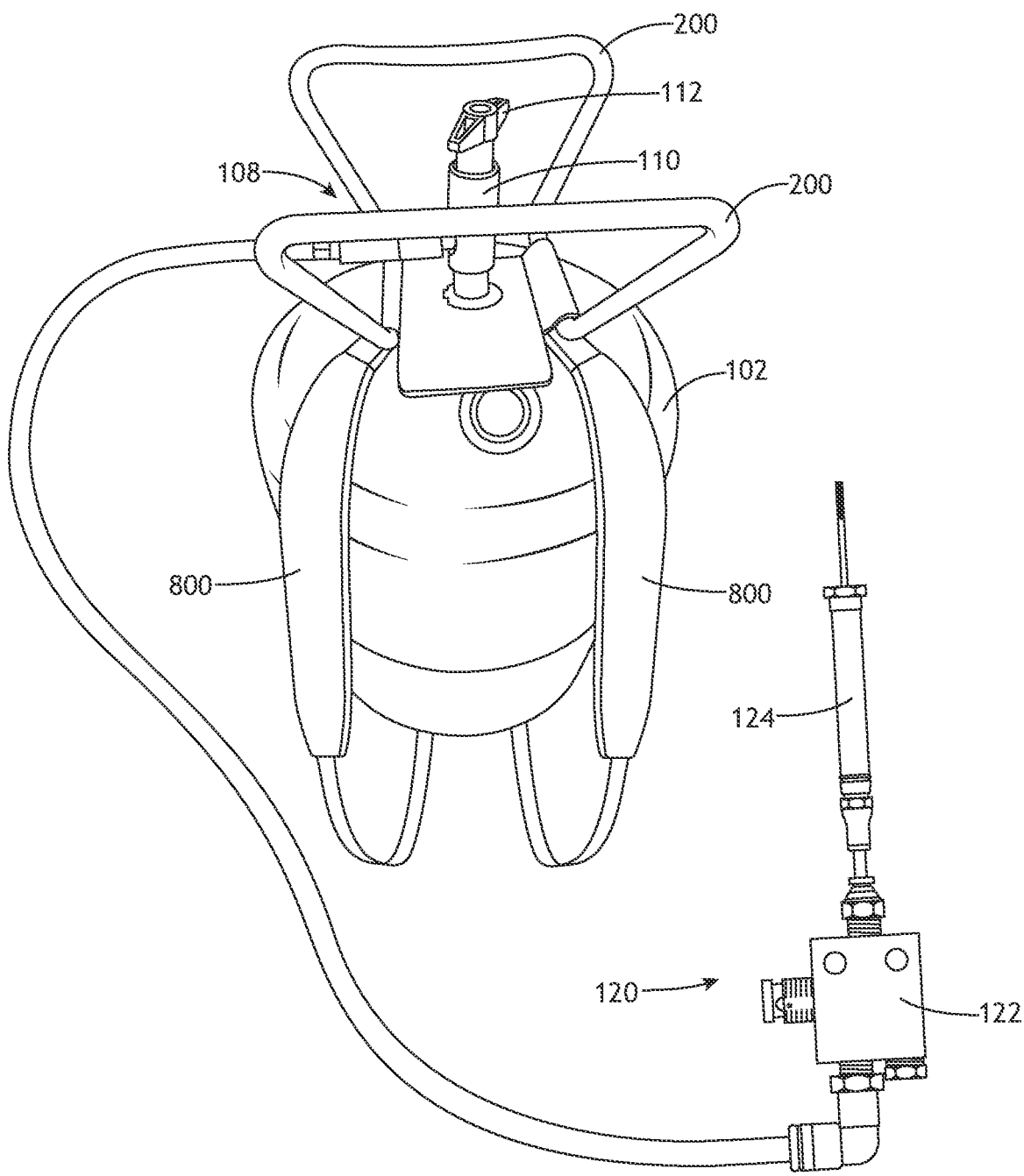
FIG. 8 illustrates a backpack for the system, in accordance with one or more embodiments of the present disclosure.

Referring to FIG. 8, the canister system 100 may be configured to couple to one or more straps 800. For example, the canister system 100 may be used as a backpack via the one or more straps. By way of another example, the canister system 100 may be carried using a cross-body strap.

It is contemplated herein that the pressurized canister 102 may include an internal bag (not shown) configured to hold the one or more liquid cleaners and the one or more propellants. The internal bag may be configured to prevent an interior surface of the pressurized canister from rusting.

Further, it is contemplated that the canister system 100 be configured to be contained within a dispensing cabinet or housing. For example, the canister system 100 may be configured to be housed within a box (e.g., a cardboard box). The dispensing cabinet may include one or more advertisements. Further, the dispensing cabinet may include promotional information. The dispensing cabinet may be configured to hold electronics and/or mechanical apparatuses to aid in the dispensing of the disinfectant/sanitizer.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A disinfectant and sanitizer canister system, comprising:
 a pre-pressurized canister, the pre-pressurized canister being pre-filled with one or more liquid cleaners and one or more propellants;
 a valve sub-system, the valve sub-system including a dispensing valve configured to couple to a portion of the pre-pressurized canister, the valve sub-system including a valve control mechanism configured to regulate the pressure of the pre-pressurized canister to cause the pre-pressurized canister to release the one or more liquid cleaners;
 a dispensing sub-system, the dispensing sub-system configured to fluidically couple the pre-pressurized canister to the valve sub-system, the dispensing sub-system comprising:
  a dispensing hose, the dispensing hose coupled to a portion of the dispensing valve; and
  a dispensing member, the dispensing member coupled to a portion of the dispensing hose, the dispensing member configured to dispense the one or more liquid cleaners contained within the pressurized canister; and
 a metering device, the metering device comprising:
  a multi-directional valve assembly, the multi-directional valve assembly including a three-way directional valve assembly including one or more valves, the one or more valves including a first valve, a second valve, and a third valve, at least one valve of the one or more valves configured to couple to a portion of the dispensing sub-system via a connector and hose, the multi-directional valve assembly including a discharge port configured to discharge a predetermined metered dose of the one or more liquid cleaners, the multi-directional valve assembly including an actuator configured to control the one or more valves; and
  a metering cylinder, the metering cylinder including a liquid side and a spring side, the spring side configured to provide a predetermined amount of pressure to dispense the predetermined metered dose of the one or more liquid cleaners.

2. The system of claim 1, further comprising:
 one or more seals, the one or more seals resistant to one or more chemicals of the one or more liquid cleaners, the one or more seals configured to couple to at least one of the metering cylinder or the multi-directional valve assembly.

3. The system of claim 1, wherein the actuator includes a push-button control actuator.

4. The system of claim 1, wherein the pre-pressurized canister includes 5% by weight propellant.

5. The system of claim 1, wherein the one or more propellants include nitrogen gas.

6. The system of claim 1, wherein the one or more liquid cleaners include didecyldimethylammonium chloride.

7. A disinfectant and sanitizer canister system, comprising:
 a pre-pressurized canister, the pre-pressurized canister being pre-filled with one or more liquid cleaners and one or more propellants;
 a valve sub-system, the valve sub-system including a dispensing valve configured to couple to a portion of the pre-pressurized canister, the valve sub-system including a valve control mechanism configured to regulate the pressure of the pre-pressurized canister to cause the pre-pressurized canister to release the one or more liquid cleaners;
 a dispensing sub-system, the dispensing sub-system configured to fluidically couple the pre-pressurized canister to the valve sub-system, the dispensing sub-system comprising:
  a dispensing hose, the dispensing hose coupled to a portion of the dispensing valve; and
  a dispensing member, the dispensing member coupled to a portion of the dispensing hose, the dispensing member configured to dispense the one or more liquid cleaners contained within the pressurized canister; and
 a metering device, the metering device comprising:
  a multi-directional valve assembly, the multi-directional valve assembly including one or more valves, at least one valve of the one or more valves configured to couple to a portion of the dispensing sub-system, the multi-directional valve assembly including an discharge port configured to one of discharge a predetermined metered dose of the one or more liquid cleaners, the multi-directional valve assembly including an actuator configured to control the one or more valves; and
  a metering cylinder, the metering cylinder including a liquid side and a spring side, the spring side configured to provide a predetermined amount of pressure to dispense the predetermined metered dose of the one or more liquid cleaners.

8. The system of claim 7, wherein the multi-directional valve assembly includes a three-way directional valve assembly including a first valve, a second valve, and a third valve.

9. The system of claim 7, further comprising:
 one or more seals, the one or more seals resistant to one or more chemicals of the one or more liquid cleaners, the one or more seals configured to couple to at least one of the metering cylinder or the multi-directional valve assembly.

10. The system of claim 7, wherein the actuator includes a push-button control actuator.

11. The system of claim 7, wherein the pre-pressurized canister includes 5% by weight propellant.

12. The system of claim 7, wherein the one or more propellants include nitrogen gas.

13. A disinfectant and sanitizer canister system, comprising:
- a pre-pressurized canister, the pre-pressurized canister being pre-filled with one or more liquid cleaners and one or more propellants;
- a valve sub-system, the valve sub-system including a dispensing valve configured to couple to a portion of the pre-pressurized canister, the valve sub-system including a valve control mechanism configured to regulate the pressure of the pre-pressurized canister to cause the pre-pressurized canister to release the one or more liquid cleaners;
- a dispensing sub-system, the dispensing sub-system configured to fluidically couple the pre-pressurized canister to the valve sub-system, the dispensing sub-system including a dispensing member, the dispensing member coupled to a portion of the dispensing valve, the dispensing member configured to dispense the one or more liquid cleaners contained within the pressurized canister; and
- a metering device configured to dispense a predetermined metered dose of the one or more liquid cleaners, the metering device comprising:
  - a multi-directional valve assembly, the multi-directional valve assembly including one or more valves, at least one valve of the one or more valves configured to couple to a portion of the dispensing sub-system, the multi-directional valve assembly including a discharge port configured discharge a predetermined metered dose of the one or more liquid cleaners, the multi-directional valve assembly including an actuator configured to control the one or more valves; and
  - a metering cylinder, the metering cylinder including a liquid side and a spring side, the spring side configured to provide a predetermined amount of pressure to dispense the predetermined metered dose of the one or more liquid cleaners.

14. The system of claim 13, wherein the dispensing sub-system further comprises:
- a dispensing hose, the dispensing hose coupled to a portion of the dispensing valve and a portion of the dispensing member, the one or more liquid cleaners configured to exit the pre-pressurized canister via the dispensing hose when the dispensing member dispenses the one or more liquid cleaners.

15. The system of claim 13, wherein the metering sub-system includes a metering cylinder including a liquid side and a spring side, the spring configured to provide a predetermined amount of pressure to dispense the predetermined metered dose of the one or more liquid cleaners.

16. The system of claim 15, further comprising:
- one or more seals, the one or more seals resistant to one or more chemicals of the one or more liquid cleaners, the one or more seals configured to couple to at least one of the metering cylinder or the multi-directional valve assembly.

17. The system of claim 13, wherein the pre-pressurized canister includes 5% by weight propellant.

18. The system of claim 13, wherein the one or more propellants include nitrogen gas.

19. The system of claim 13, wherein the one or more liquid cleaners include didecyldimethylammonium chloride.

* * * * *